US012661466B2

(12) United States Patent　　　　(10) Patent No.:　US 12,661,466 B2
Peck et al.　　　　　　　　　　　　　(45) Date of Patent:　Jun. 23, 2026

(54) SEQUENTIAL STYLET

(71) Applicants: Michael Peck, Rockville, MD (US);
Amir Fakhari, Potomac, MD (US);
Shuvodeep De, Tuscaloosa, AL (US);
Denis Alias, Silver Spring, MD (US)

(72) Inventors: Michael Peck, Rockville, MD (US);
Amir Fakhari, Potomac, MD (US);
Shuvodeep De, Tuscaloosa, AL (US);
Denis Alias, Silver Spring, MD (US)

( * ) Notice: Subject to any disclaimer, the term of this patent is extended or adjusted under 35 U.S.C. 154(b) by 774 days.

(21) Appl. No.: 17/897,110

(22) Filed: Aug. 26, 2022

(65) Prior Publication Data

US 2023/0100909 A1　　　Mar. 30, 2023

Related U.S. Application Data

(60) Provisional application No. 63/237,738, filed on Aug. 27, 2021.

(51) Int. Cl.
A61M 16/04　　　　　(2006.01)

(52) U.S. Cl.
CPC .... A61M 16/0418 (2014.02); A61M 16/0488 (2013.01); *A61M 2202/0208* (2013.01); *A61M 2202/048* (2013.01); *A61M 2205/583* (2013.01); *A61M 2205/587* (2013.01)

(58) Field of Classification Search
CPC .......... A61M 16/0418; A61M 16/0488; A61B 1/0051; A61B 1/0052; A61B 1/0057; A61B 1/008; A61B 1/009; A61B 1/01; A61B 1/267
See application file for complete search history.

(56) References Cited

U.S. PATENT DOCUMENTS

| | | | |
|---|---|---|---|
| 3,557,780 A * | 1/1971 | Sato ..................... | A61B 1/0055 600/141 |
| 3,802,440 A * | 4/1974 | Salem ............... | A61M 16/0429 138/120 |
| 5,325,845 A * | 7/1994 | Adair ................... | A61B 1/0055 604/95.04 |
| 5,358,478 A * | 10/1994 | Thompson ........ | A61M 25/0144 604/95.04 |
| 5,388,586 A * | 2/1995 | Lee ........................ | A61N 1/368 128/903 |
| 5,441,483 A * | 8/1995 | Avitall ............... | A61B 18/1492 604/95.05 |
| 5,462,527 A * | 10/1995 | Stevens-Wright ......................... | A61M 25/0147 604/95.04 |

(Continued)

FOREIGN PATENT DOCUMENTS

| | | | | |
|---|---|---|---|---|
| WO | WO-2014123473 A1 * | 8/2014 | ........ | A61M 16/0488 |
| WO | WO-2019240655 A1 * | 12/2019 | .......... | A61B 1/0051 |

*Primary Examiner* — Kathryn E Ditmer

(57)　　　　　　ABSTRACT

A Stylet device that allows for the articulation of tubing and provides a method for positioning of the tubing during intubation or other procedures while the tubing is located within a passage-way or lumen of a subject, such as an airway, organs, veins, intestines and the like. Where unique anatomical conditions are present in a subject, rendering standard intubation devices inadequate, the articulation capabilities of the apparatuses of the current invention are of particular use during methods of use and further promote the non-occlusion of the central cavity of the tube.

20 Claims, 10 Drawing Sheets

(56)                References Cited

U.S. PATENT DOCUMENTS

| | | | | | |
|---|---|---|---|---|---|
| 5,549,542 | A * | 8/1996 | Kovalcheck | ......... | A61B 1/0052 |
| | | | | | 600/150 |
| 6,033,378 | A * | 3/2000 | Lundquist | ......... | A61M 25/0147 |
| | | | | | 604/95.01 |
| 6,652,506 | B2 * | 11/2003 | Bowe | ................ | A61M 25/0136 |
| | | | | | 604/528 |
| 7,811,277 | B2 * | 10/2010 | Boulais | ................ | A61B 1/0052 |
| | | | | | 604/528 |
| 8,336,541 | B2 * | 12/2012 | Schwartz | ......... | A61M 16/0418 |
| | | | | | 128/207.14 |
| 8,409,245 | B2 * | 4/2013 | Lee | ........................ | A61B 17/29 |
| | | | | | 606/205 |
| 9,010,320 | B2 * | 4/2015 | Furman | ............ | A61M 16/0418 |
| | | | | | 128/200.26 |
| 9,375,550 | B2 * | 6/2016 | Tegg | ................ | A61M 25/0136 |
| 2005/0288656 | A1 * | 12/2005 | Koerner | ............ | A61M 25/0043 |
| | | | | | 604/95.04 |
| 2007/0156116 | A1 * | 7/2007 | Gonzalez | ............... | A61B 1/008 |
| | | | | | 604/528 |
| 2008/0236575 | A1 * | 10/2008 | Chuda | ................ | A61B 1/00052 |
| | | | | | 128/200.26 |
| 2011/0213363 | A1 * | 9/2011 | Cunningham | ..... | A61B 18/1445 |
| | | | | | 606/41 |
| 2012/0116166 | A1 * | 5/2012 | Matsuura | ............. | A61B 1/0052 |
| | | | | | 600/141 |
| 2013/0310650 | A1 * | 11/2013 | Hales | ..................... | A61B 1/267 |
| | | | | | 600/196 |
| 2013/0331825 | A1 * | 12/2013 | Mitchell | ........ | A61B 17/320016 |
| | | | | | 606/1 |
| 2016/0279365 | A1 * | 9/2016 | Esnouf | ............. | A61M 16/0418 |
| 2016/0348769 | A1 * | 12/2016 | Siegal | .................... | F16G 13/20 |
| 2017/0245933 | A1 * | 8/2017 | Graham | ................ | A61B 17/29 |
| 2018/0049623 | A1 * | 2/2018 | Golden | ............ | A61M 25/0147 |
| 2018/0250484 | A1 * | 9/2018 | McCormick | ............ | A61B 1/05 |
| 2018/0318538 | A1 * | 11/2018 | Nowlin | .................... | A61B 1/01 |
| 2019/0307979 | A1 * | 10/2019 | Karlsson | ............. | A61B 1/0052 |
| 2019/0313881 | A1 * | 10/2019 | Francher | ............ | A61B 1/00052 |
| 2021/0000336 | A1 * | 1/2021 | Maximos | ......... | A61M 16/0488 |
| 2021/0213224 | A1 * | 7/2021 | Venticinque | ...... | A61M 16/0418 |
| 2022/0218929 | A1 * | 7/2022 | Wagner | ............ | A61M 16/0488 |
| 2022/0379058 | A1 * | 12/2022 | Runnels | ................ | A61B 1/267 |

* cited by examiner

SEQUENTIAL STYLET

CROSS REFERENCE TO RELATED APPLICATIONS

This application claims the benefit and priority of U.S. provisional patent application Ser. No. 63/237,738, filed Aug. 27, 2021, which is herein incorporated by reference in its entirety.

FIELD OF INVENTION

The present invention relates generally to medical devices and procedures, and more particularly to apparatuses and methods that promote intubation of openings, orifices and/or passages (collectively referred to herein as "passage-way") in a subject by allowing insertion and effective manipulation of at least one component feature of the apparatuses in real-time, while inserted within a subject's passage-way. To further promote the placement of the tube, the manipulation capabilities allow for placement to occur without occluding the central cavity of the tube.

BACKGROUND

In the case of various situations including, without limitation, surgical procedures, non-surgical procedures and/or medical emergencies, when it has been determined that a subject (e.g., person) requires breathing assistance, a stylet is often placed inside a breathing tube (endotracheal tube) that is to be inserted into the trachea (windpipe) of a subject in order to perform what is generally referred to as an intubation or intubation procedure. An endotracheal tube is a flexible tube inserted into the trachea of a subject (patient.) Similarly, catheters and catheter devices may comprise or include a flexible tubing component for insertion into a passageway of a subject. Generally, for endotracheal applications the tube's proximal end is connected to a ventilator to supply oxygen when a patient is unable to breathe on their own due to trauma or general anesthesia (which paralyzes the diaphragm). The distal end of a breathing tube (opposite the proximal end) is generally understood to be the leading end of insertion of the tube into a subject. Beyond providing a life-saving supply of oxygen these tubes may be used for a wide range of other purposes, including the airway's visualization, foreign body removal from the trachea and protecting the airway from aspiration, and admitting sedatives. The tube's distal end is commonly provided with an inflatable cuff to prevent aspiration of gastric contents or other substances from entering the lungs.

Stylets have been known in the art to be rigid and/or flexible devices and assist users when placing an endotracheal tube into the windpipe. After the stylet is placed inside an endotracheal tube, it may allow the user to bend the endotracheal tube into a better ergonomic shape before insertion into the mouth or nose of a subject. If the shape of the breathing tube is at the wrong orientation or not in the appropriate configuration to permit entrance into the trachea and/or passage of the tube into the windpipe of a subject, then the stylet along with the breathing tube must be removed from the subject's mouth or nose, and then it must be reshaped prior to performing another attempt (insertion) at the placement of the endotracheal tube into the trachea/windpipe.

The process of removing the breathing tube from the mouth or nose to reshape it and then reinserting back into the mouth or nose is time-consuming, can result in damage to the oral tissues, drop in oxygen levels and with each attempt, the likelihood of success decreases. Minimizing these complications will reduce or prevent episodes of cardiac arrest, brain injury, death, and with the recent pandemic, the spread of pathogens. Thus, the delay and/or failure in placement of a breathing tube in a subject can turn a lifesaving procedure into one that is life-threatening. It has been estimated that deaths associated with intubation due to lack of oxygenation is 2-3%. It has also been reported that up to 40% of intubations in intensive care units are not successful on the first attempt.

Over the years there have been numerous devices created in order to aid in the placement of a breathing tube. Under optimal conditions and where the anatomy of the patient allows for optimal alignment a stylet user will experience prime visualization of the trachea and if the endotracheal tube is in proper alignment with the trachea then placement of the breathing tube will be seamless. Often intubation is being attempted under sub-optimal conditions. This is challenging, especially in emergencies, presumed easy intubations or patients with anatomical difficulties, such as anterior glottis or target orifice. In many emergent scenarios complications arise due to unpredictable irregularities in the patients positioning, discrepancies of the anatomy such as the orientation of the tracheal opening between the vocal chords (commonly referred to as the "glottis") and the type of emergency. The anatomies of subjects may differ significantly and the critical part of the intubation process is to ensure that the tip (distal tip or end) of the tube is placed correctly inside the trachea and the intubation is performed in a timely manner.

In such cases, improper insertion of the tube through the opening can cause severe injuries and even death due to lack of oxygen. The standard practice in such cases is to insert a stylet into the endotracheal tube's lumen, which helps to bend the tube and thus improve the chance of passage of the tube through the tracheal orifice. Although this method is currently used, it has several limitations, including the visualization of the insertion path and the subsequent removal of the stylite stylet from the endotracheal tube. Once the stylet is bent, it must retain that shape to maintain the correct configuration. However, this puts the patient at risk due to delays in providing oxygen.

The introduction of devices like video laryngoscopy that have been provided in the past can be very helpful in increasing the ease of placement due to improved visualization. Even with advancements like this, it can still be difficult to place an endotracheal tube due to the unpredictability of variations of the human anatomy. For example, a medical professional can have a significantly clear view of the vocal cords and the entrance to the trachea but due to the inability to properly change the direction(s) of the endotracheal tube it makes placement of the tube in the windpipe substantially and/or significantly impossible. Under these suboptimal conditions placement of a lifesaving breathing tube becomes a matter of life or death and thus changes a routine scenario to an urgent or emergent one. In these often unpredictable circumstances, there arises a need to manipulate the shape of at least a part or section of the endotracheal tube to permit insertion past the vocal chords.

The need for tubing and devices that promote the intubation of subjects has only increased over the years. Today, assuming 50,000,000/yr surgical procedures taking place in the United States with a 32% usage of a stylet for general anesthesia, this equates to approximately 12.8-15 million potential instances of need. Further, currently, it has been estimated that approximately 250,000/yr intubations in emergency situations are occurring. With these types of volumes of need, it is unfortunately common that the cost of many of the current stylet devices can present significant economic challenges for users, in all situations, to obtain these types of necessary, life-saving devices. It is also generally understood that all of these potential intubations do not occur under optimal conditions. Subjects have different anatomical considerations based on discrepancies in structure or even simply based on the age of the subject. Endotracheal tubes come in different sizes, and the size used is chosen based on the age, sex, and bodyweight of the patient. Typically, the tube's diameter is 7-7.5 mm in the case of women and 8-9 mm in case of men. In the case of newborns, the diameter is 3-3.5 mm. The tube is made of flexible materials, commonly comprised of latex free materials. Currently, it can often be the case that a particular stylet device has significant limitations in its use with various subjects that have significantly varying anatomical and/or other considerations.

The continued gap in medical advancement in the intubation process even with ideal anatomical sight lines has led to the need to develop a new mechanism for implementation and use in various circumstances including, without limitation, in routine, surgical or emergency situations. Today, there remains a need for a stylet device with the real-time capability to modify its shape and thus its direction, without the need to remove, reshape and then re-attempt insertion of the device during a procedure. There further remains a need for a device that is capable of being used with various different subjects and varying anatomical considerations. There further remains a need for a device that can be provided with improved economic considerations to promote improved access to these types of life-saving devices by users. Thus, the need remains for an improved stylet device that at least promotes the optimization of the user experience, improvement in ease of intubation procedures, reduction in exposing a target subject to delay and harm, and affordability and ease of access by users. The current invention can address these needs and potentially other needs of users and subjects.

SUMMARY OF INVENTION

In exemplary embodiments of the current invention, the apparatus (referred to herein as "Stylet") is comprised of a rigid yet malleable and compliant handle and shaft. As contemplated for any exemplary embodiment of the current invention, the Stylet can be inserted and take the shape of the inside walls of an Endotracheal Tube to match the Endotracheal Tube Magill Curve. Further, for any exemplary embodiment of the current invention, at least a portion of the shaft may be at least partially encompassed by a sleeve or sheath assembly to promote the effective use of the stylet device.

In an exemplary aspect, a Stylet can consist of a single unit Stylet which comprises a user manipulated handle assembly connected with a shaft that ends in a tip opposite the connection of the shaft with the handle assembly. It is contemplated that the shaft may be detachable from the handle assembly or integrated providing a body/handle assembly. The tip of the shaft of the Stylet can be manipulated through a mechanism. The mechanism is in operational connection with and can be interacted with by a user through the handle assembly. The directionality or movement profile (geometry) of the tip may be one which is pre-designated through a mechanism, such as one single lever motion, button press, handle squeeze, or it may be one which contains several mechanisms combined to perform independent actions of tip movement in independent directions. The operational connection of the handle assembly with the geometry of the tip may be provided by a manually driven mechanism or a mechanically driven mechanism. It is contemplated that the mechanically driven mechanism may be comprised of one or more component features, such as a motor, hydraulic mechanism, semiconductors, and/or electronics. The manipulation of the Stylet tip may also be accomplished through the implementation of one or more automated mechanisms which may also be interfaced with various other devices, such as an onboard camera or external camera to perform hands free intubation.

In exemplary embodiments of the current invention, a Stylet generally comprises a handle assembly that is connected, via a shaft, to a tip, wherein the handle assembly can be interacted with by a user and the tip, and at least a portion of the shaft, may be insertable within a lumen of an endotracheal tube. Therefore, it is contemplated that at least a portion of the Stylet can be received within the central cavity of the endotracheal tube. The distal end of the Stylet consists of geometry which can be manipulated, via a mechanism, to bend an end (distal end) of the endotracheal tube. Thus, via the mechanism, the Stylet is enabled to manipulate an articulable portion of the tip providing a change in the position of the tip relative to the rest of the shaft. As indicated, it is contemplated that the mechanism allows manipulation of the geometry of the tip between numerous and various positions on an intermittent or continuous basis as determined by the user. The mechanism(s) for providing this manipulation capability may be any one or combination of those described herein.

In another exemplary embodiment of the current invention, the shaft of the Stylet can comprise a first section, an intermediate section and a second section. The first section may be generally understood and referred to herein as the proximal end that connects to a handle assembly and the second section may be generally understood and referred to herein as the distal end. The intermediate section connects with the first section at one end and the second section at the end opposite therefrom. The connection between any of these sections can be static (non-moveable) or articulable using known connection technologies. The Stylet may be employed with an endotracheal tube wherein it is contemplated that at least one of (i) the intermediate section and second section; (ii) a portion of the intermediate section and the second section; or (iii) a portion of the second section of the Stylet may be insertable within a lumen of the endotracheal tube. Therefore, it is contemplated that at least a portion of the shaft of the Stylet can be received within the central cavity of the endotracheal tube. The distal end of the shaft of the stylet consists of geometry which can be manipulated to bend the distal end of the endotracheal tube. The distal end of this body may also contain geometry which can provide additional degrees of freedom to the deflection of the endotracheal tube. A mechanism implemented as part of the Stylet provides an operational connection to at least a portion of the second end. This portion of the second end is referred to herein as an articulable portion. Thus, via the mechanism, the Stylet is enabled to manipulate the articulable portion providing a change in the position of the second end relative to the first end. As indicated, it is contemplated that the mechanism allows manipulation of the geometry of the second end between numerous and various positions on an intermittent or continuous basis as determined by the user. The mechanism(s) for providing this manipulation capability may any one or combination of those described herein below.

The current invention contemplates and provides various apparatuses and features as described herein. Any and all such apparatuses may be employed individually and in any combination. Various contemplated features that relate to any of the exemplary aspects may be incorporated into any one or more of the exemplary embodiments. Thus, any refinements and additional features may exist individually or in any combination with any aspects of the various exemplary embodiments. It is contemplated that the advantages from any such refinements and additional features will be apparent from the drawing figures and the description provided herein below.

DETAILED DESCRIPTION

Figure 1:
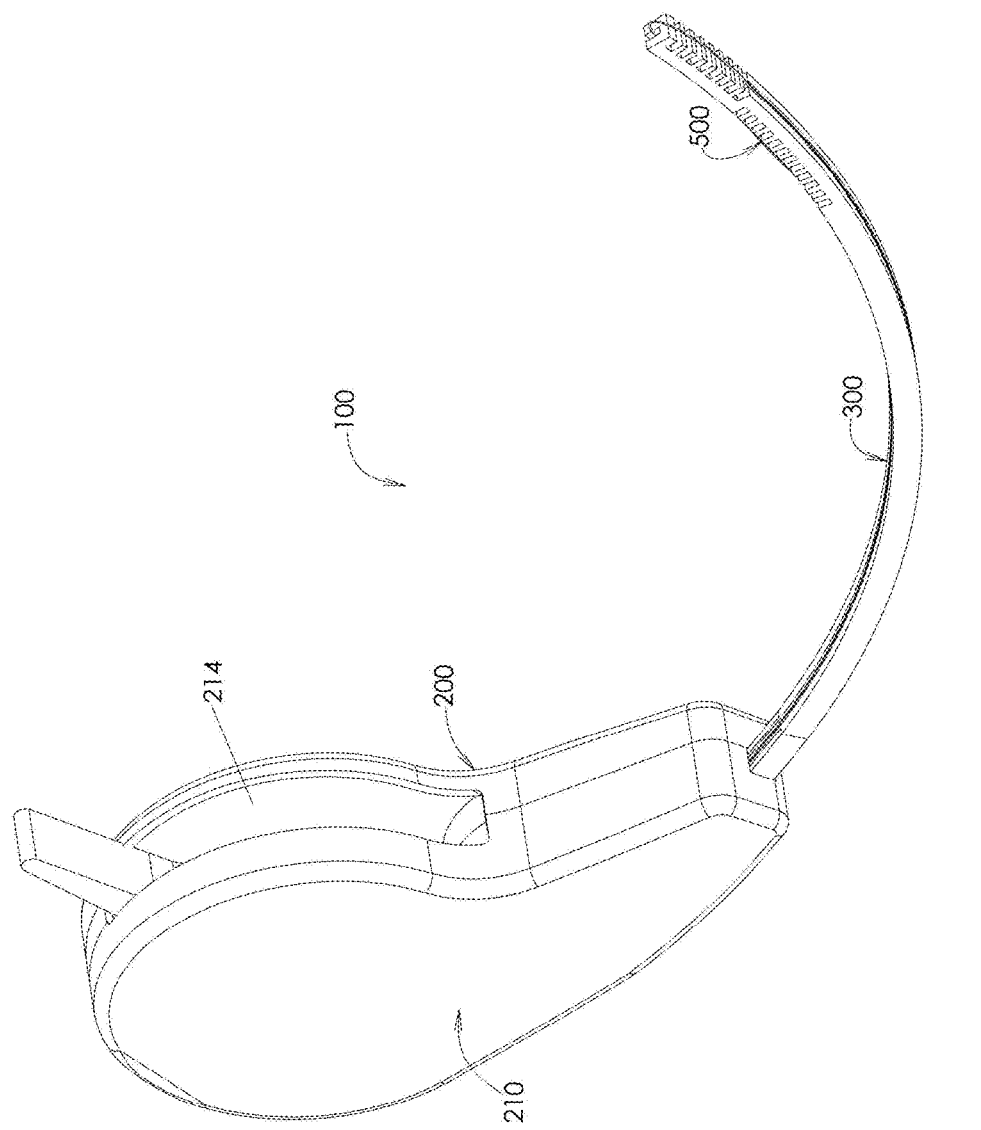
FIG. 1 is an illustration of a Stylet in accordance with an exemplary embodiment of the current invention.

FIG. 1 shows a first exemplary embodiment of a Stylet 100 incorporating features of the invention as shown in FIGS. 1 through 6. In the exemplary embodiment shown, Stylet 100 comprises a handle assembly 200 housing a Sequential Tip Shaping Mechanism 400 (see FIGS. 3 & 4) and connected with a Shaft Assembly 300 that is also connected to a Tip Assembly 500 (see FIGS. 5A & 5B). In another exemplary embodiment shown in FIG. 6, a Stylet 600 comprises a second handle assembly also housing a Sequential Tip Shaping Mechanism (not shown) and connected with a Shaft Assembly connected to a Tip Assembly. The various assemblies, mechanisms, features and/or components of the exemplary embodiments of the Stylet shown will be described in detail herein below. It is contemplated that the various assemblies, mechanisms and component features of the current invention can be integrally formed or removably connected to one another using various connection technologies. It is further contemplated that differently configured assemblies, mechanisms and component features can be interchangeably connected to establish an embodiment of the current invention. In order to promote the ease of use for any of the embodiments of the current invention any aspect can be disposable or reusable. It is understood that any description provided including, without limitation, any alternative, additional or modifications described shall be available and able to be applied to any embodiment.

The handle assembly 200 is connected to, engages with and/or operationally interacts with the sequential tip shaping mechanism 400. This operational interaction can be enabled through the connection of various component features of the handle assembly 200 with various component features of the sequential tip shaping mechanism 400. The connections established between the various component features can be made through the use of various connection technologies and provide for the removable connection between the component features. It is further contemplated that various component features of the handle assembly 200 and sequential tip shaping mechanism 400 may be integrally formed with one another. Still further, the current invention can be enabled with a handle mechanism that comprises all component features that enable the operational capabilities of both the handle assembly and sequential tip shaping mechanism.

The shaft assembly 300 includes a shaft 305 having a first segment 308 terminating at a first end 310 that is connected to, engages with and/or operationally interacts with the handle assembly 200 and sequential tip shaping mechanism 400. A second segment 312 terminating at a second end 314 is connected to, engages with and/or operationally interacts with the tip assembly 500. It is contemplated that various exemplary embodiments of the current invention may comprise a fully integrated shaft mechanism comprising all component features and functional capabilities described herein for the shaft assembly 300 and tip assembly 500. In such embodiments, opposite the end that comprises the tip assembly is a first end that operationally engages with the handle assembly 200 or handle mechanism as described herein below.

Figure 6:
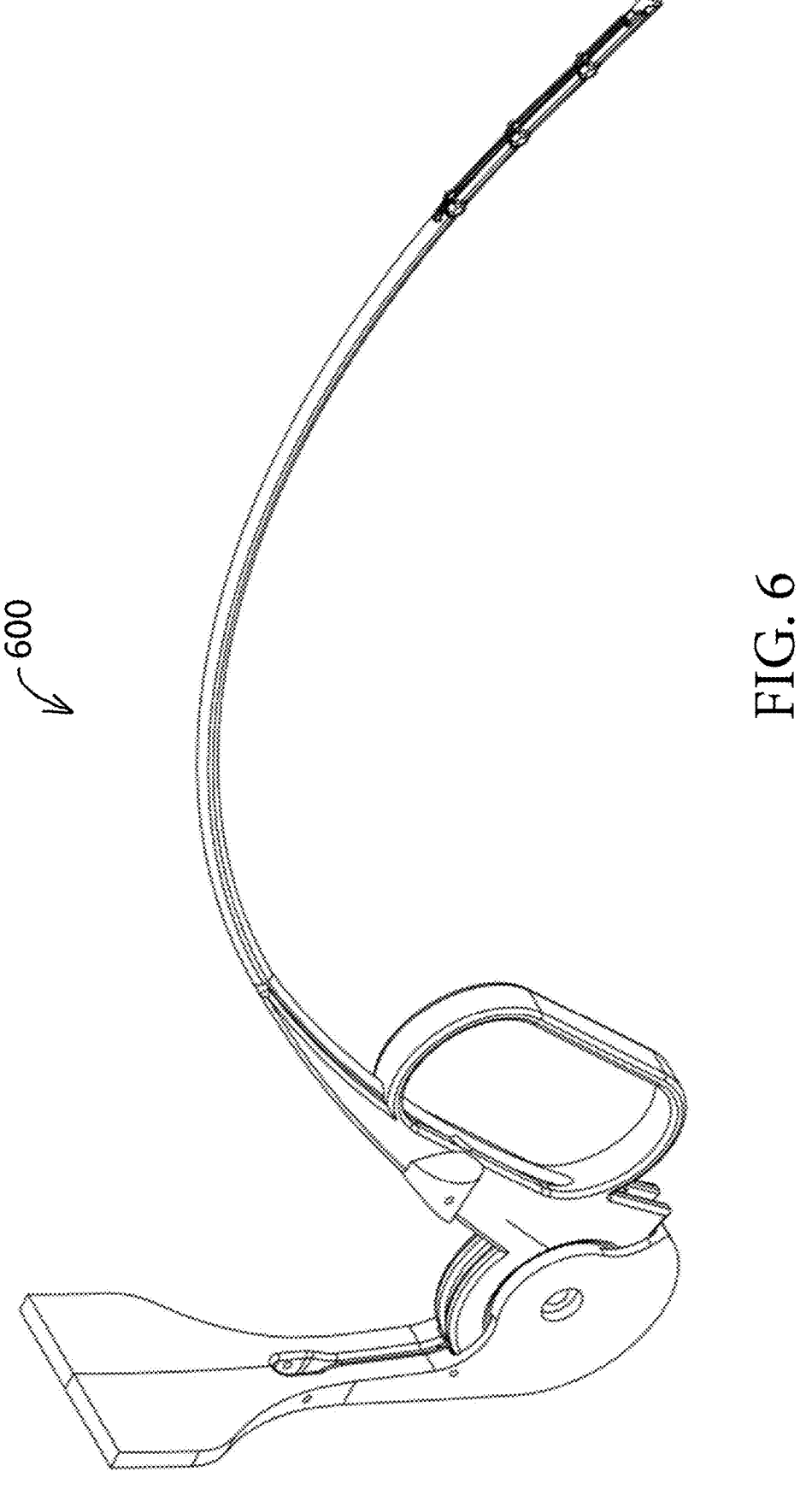
FIG. 6 is an illustration of a Stylet including a second handle assembly in accordance with an exemplary embodiment of the current invention.

In the exemplary embodiments shown in FIGS. 1 & 6 the shaft 305 is insertable into and removable from the housing 210 through shaft receiver 215. In these embodiments, it can be understood that at least a portion of the first segment 308 is inserted through shaft receiver 215 into the housing 210. The first end 310 of shaft 305 is inserted into the housing 210 until it is positioned to promote the operation of the capabilities provided by the current invention. In current embodiments, the first end 310 is positioned proximal to a first filament connector 412 and second filament connector 444. It is contemplated that the position of shaft 305 within housing 210 can be varied without departing from the scope and spirit of the current invention. It is contemplated that the shaft assembly 300 can be removably connected with the tip assembly 500 using various connection technologies. Still further, exemplary embodiments of the current invention can be enabled with a fully integrated shaft mechanism that comprises all component features that enable the operational capabilities of both the shaft assembly 300 and tip assembly 500 and may operationally engage with the handle assembly 200 in any manner contemplated by those skilled in the art.

Figure 2A:
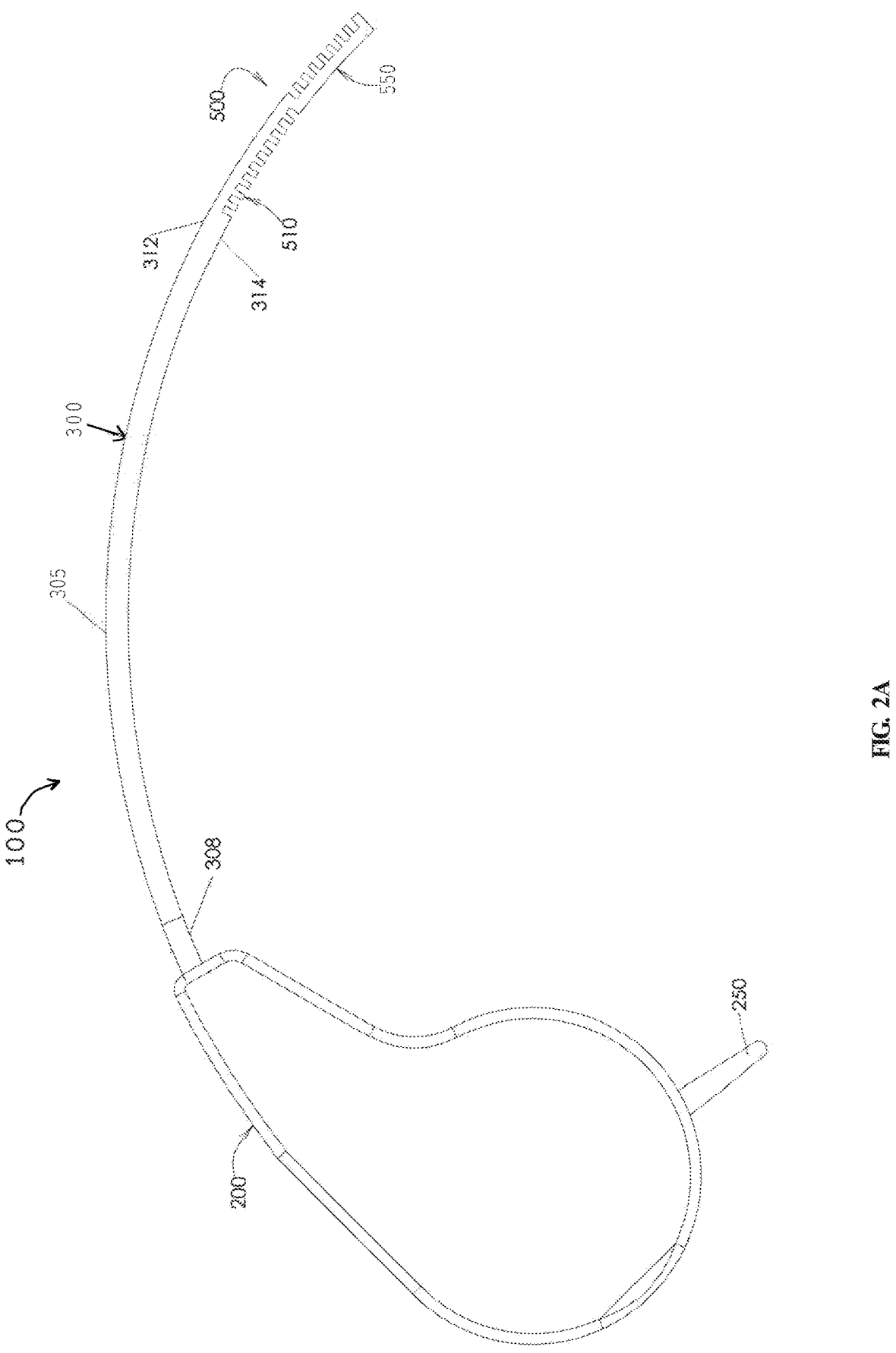
FIG. 2A is an illustration of the Stylet wherein a grip of a handle assembly and a tip is shown in a first, neutral position in accordance with an exemplary embodiment of the current invention.
Figure 2B:
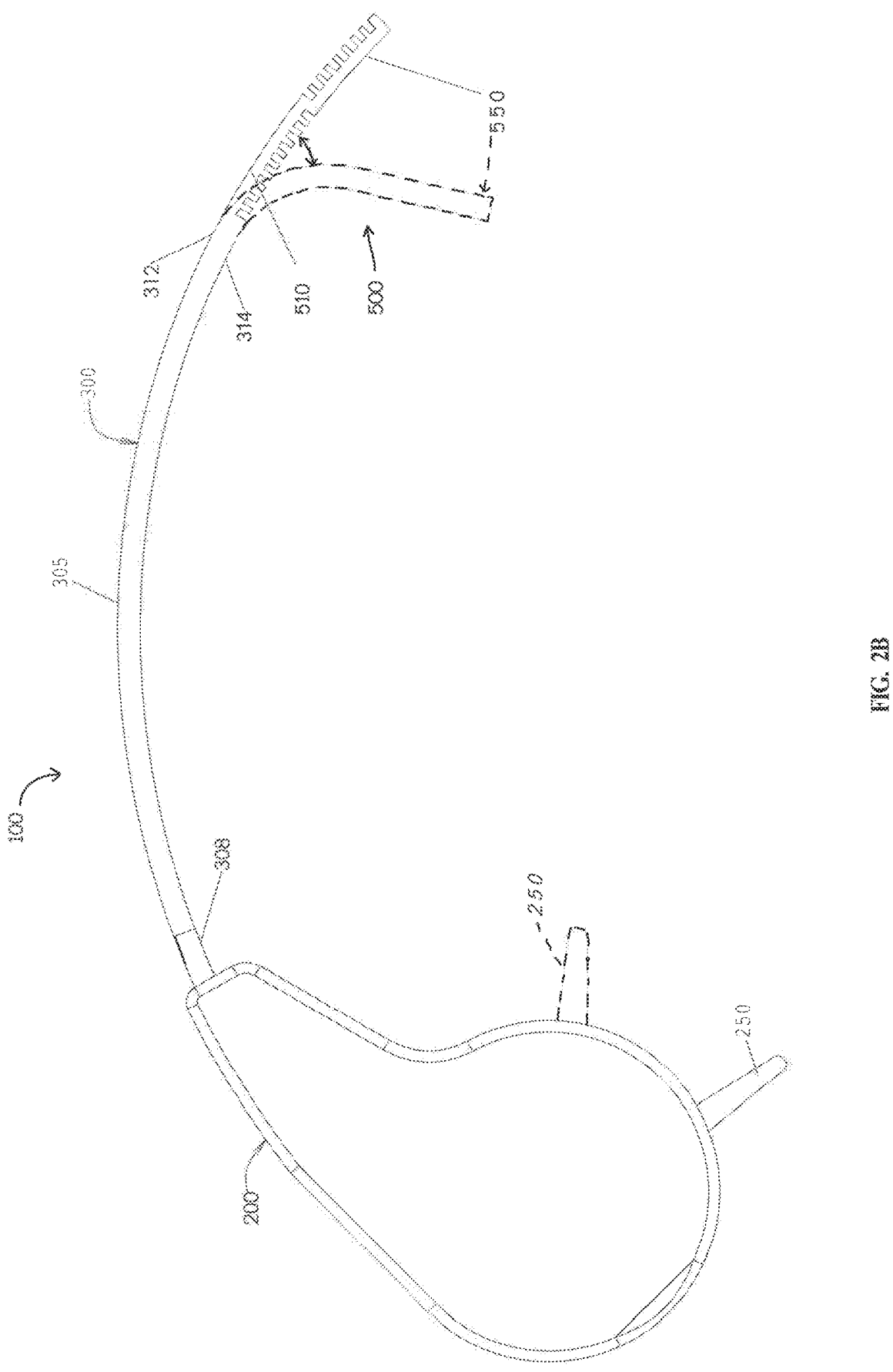
FIG. 2B is an illustration of the Stylet wherein the grip of the handle assembly and the tip is shown established in a second position (the "C" shape position) in accordance with an exemplary embodiment of the current invention.
Figure 2C:
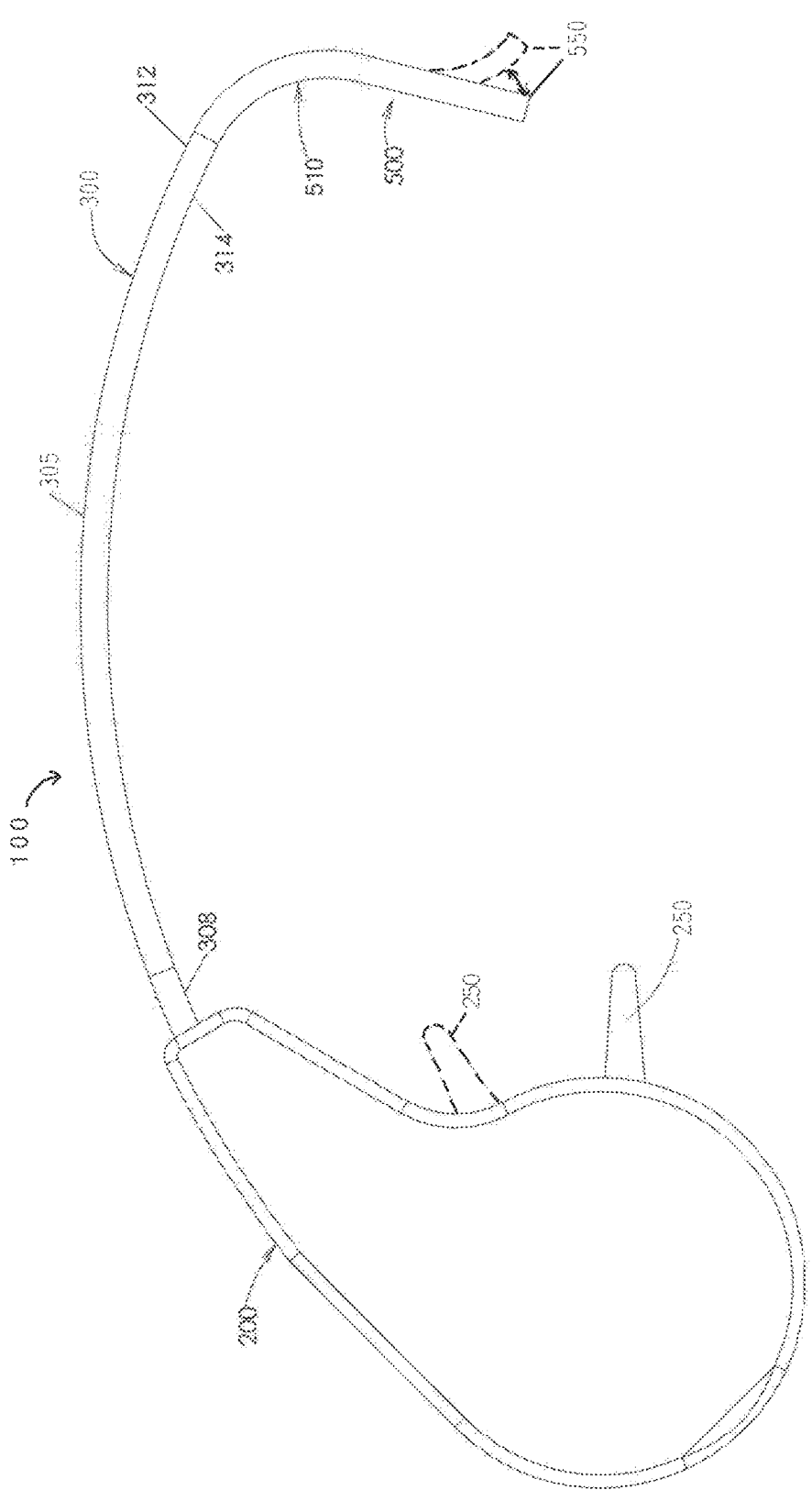
FIG. 2C is an illustration of the Stylet wherein the grip of the handle assembly and the tip is shown established in a third position (the "S" shape position) in accordance with an exemplary embodiment of the current invention.

Any of the various embodiments and configurations established for the handle assembly, sequential tip shaping mechanism, shaft assembly and tip assembly whether established as separate or integrated components and including, without limitation, all component features, that comprise and enable the operational capabilities of the current invention are implemented to provide a stylet device with an articulation capability that enables the manipulation of tip geometry while the device is in use and in-situ. In general, this articulating or bending capability of the tip is promoted and can be performed through a single handle action, which can be continuous or intermittent, as shown in FIGS. 2A, 2B and 2C described herein below. With a starting position shown in FIG. 2A, as the stylet user activates the handle (applies a force to the handle and moves the handle), the handle assembly 200 and sequential tip shaping mechanism 400 via shaft assembly 300 deforms the tip 500 geometry to a shape shown in FIG. 2B. This can be followed by further deformation of the tip 500 shown in FIG. 2C, thus completing the desired tip movement.

As shown in FIGS. 1-4 the handle assembly 200 comprises a housing or body 210 having a first section 211 and a second section 212 that can house various mechanisms and component features within. First and second sections of housing 210 are removable from and connectable to one another. This connectivity can be accomplished utilizing various mechanical means as contemplated by those skilled in the art. It is further contemplated that the housing 210 may be formed and established with a significantly integrated connection between the first and second sections.

The configuration of housing 210 can provide an outer shell and define an interior space within having various shape and dimensional characteristics designed to accommodate the component features of the current invention to be housed within. It is further contemplated that the configuration can be established to address specific ergonomic considerations. The body 210 is further configured with a handle travel guide or grip travel guide 214 which promotes and enables the operational movement of a handle or grip 250. This operational movement is further described herein below in reference to FIGS. 2A-2C and the manipulation of tip geometry provided by the current invention. At least a portion or segment of the handle 250 extends from the housing 210 to promote and allow for user interaction and application of force to the handle 250 enabling operation of the stylet device. The handle may be removably connectable or integrally formed with the various other component features of the current invention. Formed within housing 210 is the shaft receiver or shaft insertion point 215 through which at least a portion of shaft 305 is inserted within the interior of the housing 210 and enabled to operationally interact with the sequential tip shaping mechanism or assembly 400.

The shaft receiver 215 may be further configured to comprise or have in close proximal relation to it a mechanism or multiple mechanisms by which the position of shaft 305 relative to the housing 210 and handle 250, when shaft 305 is fully or partially inserted into an operational position within the housing 210, may be significantly affixed or promote the fixation of a position for shaft 305. It is contemplated that the dimensional configuration established for the shaft receiver 215 may vary to accommodate varying sizes and shapes of shaft assemblies. In an exemplary embodiment one or more compression locking mechanisms may be included (not shown) in or proximal to the shaft receiver 215. Thus, as the shaft 305 is inserted within the housing 210 through the shaft receiver 215 any one or more of the compression locking component features may engage with or along any point of the shaft 305 to promote a securing of the position of shaft 305 within housing 210. Shaft 305 may further comprise significantly complementary component features that promote securing of the position of the shaft 305 when inserted in housing 210 by engagement with the compression locking component features. It is contemplated that alternative connecting or locking mechanism may be employed lo enable the securing of the position of a shaft when inserted through the shaft receiver into the housing of an exemplary embodiment of the stylet of the current invention.

Figure 3:
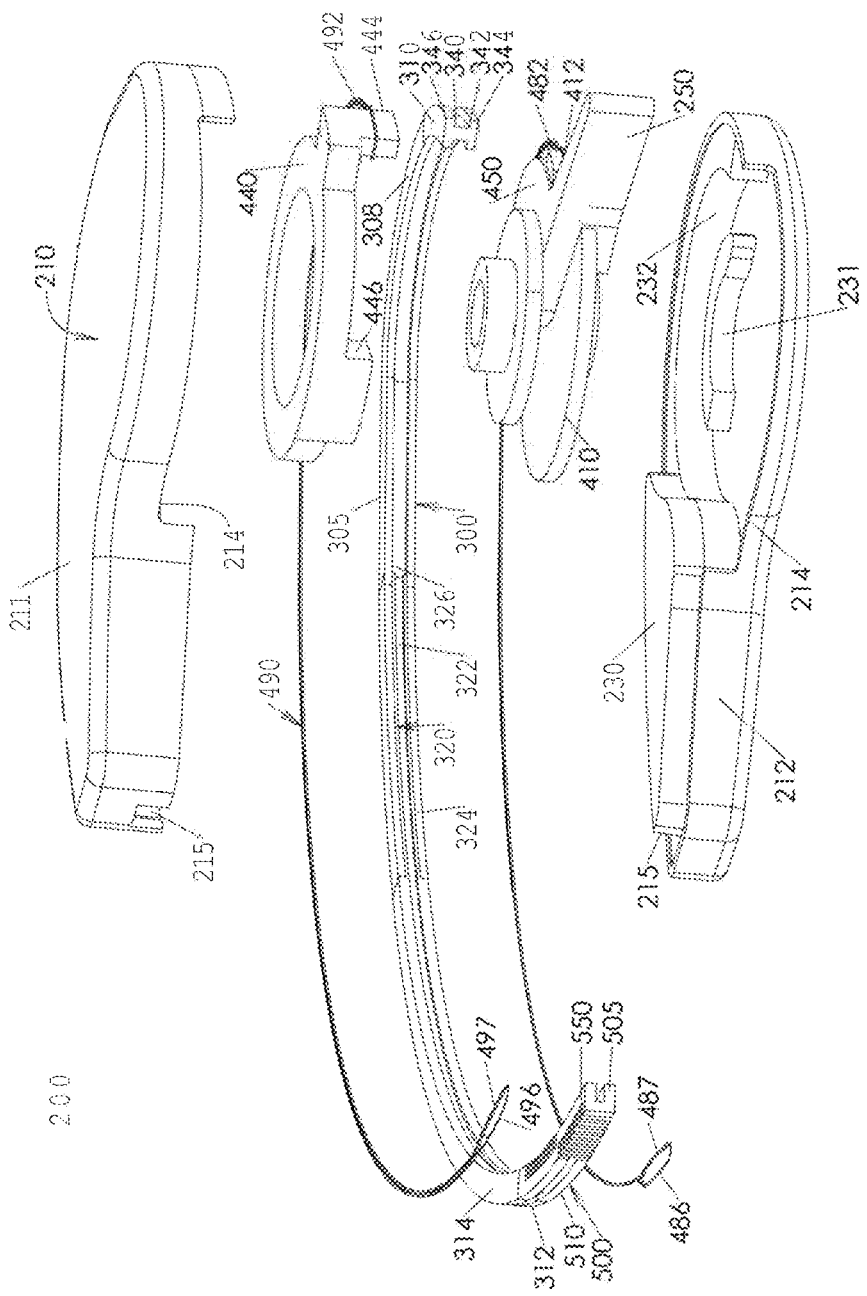
FIG. 3 is an illustration of an exploded view of the Stylet in accordance with an exemplary embodiment of the current invention.
Figure 4:
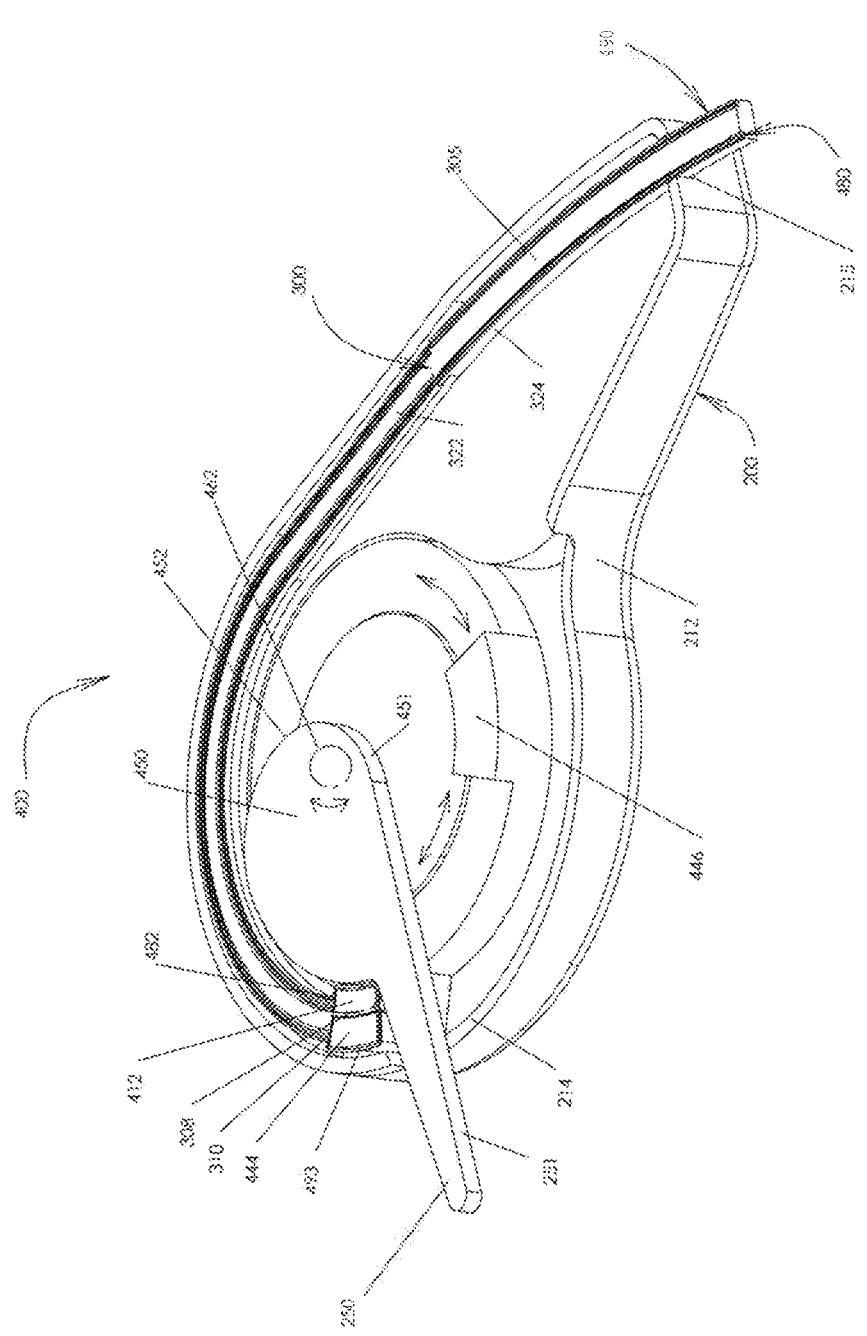
FIG. 4 is an illustration of a cut-away view of the handle assembly and a sequential tip shaping mechanism contained therein in accordance with an exemplary embodiment of the current invention.

As shown in FIGS. 3 & 4 the interior space defined by housing 210 can comprise a first shaft support construct 230 that provides structural integrity support to the housing 210 and a guide for the segment or portion of the shaft 305 that is inserted within the housing 210 through shaft receiver 215. Further, the first shaft support construct, during the tensioning of the first filament 480 (described herein below) provides a pivot point 460 (dashed lines) about which the rotation of the first filament 480 is promoted as a first tensioning force increases and decreases. The pivot point can be established in various positions as determined by the operational needs of an exemplary stylet device. A handle rotation support 231 can be established in the interior space of housing 210 to provide support for the rotational operation of handle 250. A sequential support 232 can be established in the interior space of housing 210 to provide support for the operation of the handle 250 and the application of force to the tip articulating component feature as will be described herein below.

The dimensional configuration (size and shape) and interaction with other component features of this first shaft support construct 230, handle rotation support 231 and sequential support 232 can vary as contemplated by those skilled in the art to promote and/or provide the stylet with its functional capabilities. It is contemplated that the positioning of the various elements of the handle assembly 200 may be positioned in various locations relative to the various elements, aspects and features comprising the handle assembly 200. Further, the various elements, aspects and/or features of the handle assembly 200 may be removably connectable with one another using various connection mechanisms and technologies. It is further contemplated that one or more of the various elements, aspects and/or features may be integrally formed with any other element, aspect and/or features.

The shaft assembly 300 can comprise shaft 305 that can be significantly configured in an "H" shape. It is contemplated that the shaft assembly and tip assembly are similarly configured and as such the tip assembly 500 is established in a generally "H" shaped configuration. In the alternative, the shaft and tip assemblies may be configured in various forms having different types of cross sections including, without limitation, a circular, square/rectangular, hexagonal or other configuration. Generally, this configuration allows for the operation of the sequential tip shaping mechanism 400 more particularly, in the exemplary embodiment shown and described herein, the "H" shaping provides shaft 305 with a first channel 320 and a second channel 340. Further, it is contemplated that a sleeve or sheath assembly may be engaged with at least a portion of the shaft for any shaft assembly. The sleeve or sheath assembly may promote the efficient and effective operation of one or more functions of exemplary embodiments of the current invention. As will be further described herein below, when tensioning forces are generated during the use of a stylet of the current invention, the sheath or sleeve assembly may promote the operation of one or more component features of the sequential tip shaping mechanism 400. For instance, the sheath or sleeve assembly may promote a filament's operational engagement and proper positioning relative to a channel of the shaft assembly. It is further contemplated that a sheath or sleeve assembly may promote the insertion in and interchangeability with a handle assembly of one or more exemplary stylet devices.

The first channel 320 can be understood as being established in a top side or anterior side of shaft 305 while the second channel 340 can be understood as being established in a bottom side or distal side of shaft 305. The first channel 320 has a bottom wall 322 and is connected with a first side wall 324 and second side wall 326 opposite the first side wall 324. These walls form an open channel within which a first filament 480 (FIG. 3) can be positioned and the functional capabilities of the stylet 100 can be supported. The second channel 340 has a bottom wall 342 and is connected with a first side wall 344 and a second side wall 346 opposite the first side wall 344. These walls form an open channel within which a second filament 490 (FIG. 3) can be positioned and the functional capabilities of the stylet 100 can be supported.

Shaft assembly 300, including shaft 305, may have various overall dimensional characteristics. The overall length established for a shaft employed with the current invention may range from twelve (12) inches to thirty-six (36) inches or have another length as contemplated for use. The height or thickness dimension may range from 4 millimeters to one inch and length may range from 6 inches to 24 inches. In the current exemplary embodiment, the thickness dimension of the bottom wall may range from 0.5 millimeter to 2 millimeter. The thickness dimension of the side walls may range from 1 millimeter to 2 millimeters. The dimensional configuration and shape given shaft 305 may vary significantly in various contemplated embodiments without departing from the scope and spirit of the current invention. In the current embodiment, the bottom wall 322 and 342 are integrally formed and provide the framework for the channels that extend the length of shaft 305. The first and second side walls for both channels are integrally formed with their respective bottom walls. It is contemplated that the bottom walls, first side walls and/or second side walls may be formed through a connection mechanism and, further, may be removably connectable with one or more of the various component features.

As shown, shaft assembly 300, including shaft 305, can be configured with an overall curvature, are or angular profile that is conducive to and promotes the operational effectiveness of the stylet device. The angular profile established for a shaft of a shaft assembly may range from 0.1 degrees to 20 degrees of arc. The material composition of shaft 305, and of stylet 100 and 600, can be made of any material sufficiently malleable to promote the operation of the stylet and hard and strong to withstand the forces applied during operation. Contemplated for use with the current invention are various forms of medical grade material is including, without limitation, plastic(s), polyethylene, polypropylene, recyclable/sustainable materials and such other materials as may be contemplated by those skilled in the art. In an alternative embodiment the shaft may be fabricated in the shape of a hollow, semi-rigid, tubular form which is generally circular in transverse cross-section. The hollow traversing the length of the shaft. The hollow may generally include one or more channels established within.

The Stylet 100 allows a user to manipulate an endotracheal tube tip in a sequential manner with a single handle motion. In FIG. 2A the Stylet 100 is established in an initial position. In this position the grip 250 of the handle assembly is in a first position and the shaft 305 is shown in a first position. In this positioning, the first and second sections of the tip 500 (see FIGS. 5A & 5B) can be seen to be established in a non-deflected or articulated position relative to one another and the remaining body of the shaft. In this regard, the grip 250 is in the first (static or neutral) position when no force is being applied to push the grip 250 along or down the grip guide 214 toward the shaft 305. Further, in this static or neutral position it is understood that the tension (initial tension) in the first filament 480 and second filament 490 is minimal.

In FIG. 2B, the tip 500 is shown as being established in a first deflected or articulated position. This first deflected position is promoted and accomplished by engaging the grip 250 in the first grip position and, through application of force (pushing) to the grip 250, moving the grip 250 further down the grip guide 214 to shaft 305, thereby, repositioning grip 250 to the second grip position. In exemplary embodiments, the force applied lo the grip is from a user. As seen by the dashed lines in FIG. 4, a grip rotation pin 452 provides for an operational connection between grip 250 and one or more of the other support guides within housing 210. The grip rotation pin 452 further promotes and enables the rotation of handle 250 when the user applies a force or pushes on the handle 250. This rotational movement of grip 250 promotes a first rotational force that is translated to a first shaping component 410 of the sequential tip shaping mechanism 400 (see FIGS. 3 & 4).

This user applied force can promote the rotational movement of grip 250 along the grip guide 214 established by the housing assembly 200 in housing body 210. The user translated force through the grip 250 rotates the grip 250, a nautilus member 450 that is integrally formed in grip 250 and the first shaping component 410. Through the nautilus member 450 and first shaping component 410, which is connected to the first filament connector 412, the first rotational force applies a rotational force to a first filament connector 412 connected to the first shaping component 410. The first filament connector 412 is operationally connected with a first end 482 of the first filament 480. This operational connection, in the current embodiment, is provided by the first end 482 being established in a first loop 484 configuration. The first loop 484 is then engaged (wrapped) around the first filament connector 412. Thus, as the first rotational force from engagement with grip 250 is translated into the rotational movement of first filament connector 412 a tensioning force is applied to the first filament 480. Further, from the rotational movement imparted via the grip 250 through the nautilus member 450 the application of the tensioning force to first filament 480 is further supported and/or promoted. This tensioning force is translated along the length of first filament 480 to second end 486. A second loop 487 configuration is established in second end 486. Second loop 487 is configured to operationally connect and engage with first section 510 of tip 500. As the tensioning force applied to first filament 480 increases due to user engagement with grip 250, thereby moving or rotating grip 250 from the first grip position to the second grip position, application of the first rotation force is translated into first section 510 of tip 500. This tensioning force causes the second loop 487, through engagement with at least the shaping form 539, to apply a deflection force to first section 510 of tip 500. It is contemplated that second loop 487 may apply a deflection force to first section 510 of tip 500 through engagement with any one or combination of shaping forms 531 through 539. The application of the deflection force to first section 510 causes tip 500 to articulate an angular amount, as denoted by the theta symbol in FIG. 2B, from the first position established by the tip 500 in the non-deflected position into a second position (primary arcuation).

It is understood that the angle of articulation imparted to the first section 510 can vary and may be dependent on the amount of force applied to grip 250 by a user. The degree of articulation (deflection) imparted to first section 510 may be varied by varying the position of the grip 250 relative to the grip guide 214. When grip 250 is pushed, establishing a curvature for the first section 510 of tip 500 it can be understood that the tip 500 is in primary arcuation. Releasing the grip 250 and returning it to its static, neutral position allows the curvature to be released from the first section 510 of tip 500 of the stylet 100. Tip 500, in operation with an endotracheal tube, when articulated into the second position, can press against the interior sidewall of the tubing within which stylet 100 may be at least partially inserted (e.g., endotracheal tube) forcing the tubing to conform with the second position established by tip 500.

Thus, the first step in the sequence of events of this mechanism includes the real-time deflection of a fixed length (denoted as first section 510) of the stylet tip assembly 500, and thus the tip of the endotracheal tube it is within, in an anterior direction (towards the center of curvature of the major radius, denoted $\theta_1$ in FIG. 2B). The deflection of this tip in the anterior direction is achieved by the movement of the grip 250 from the first (static/neutral) position to a second (intermediate) grip position of the full grip stroke. The full grip stroke being denoted by the travel of the grip that is allowed and enabled by grip guide 214. The completion of this first step promotes and can achieve a "C" shape of the tip assembly 500 of the stylet 100 and any endotracheal tube within which it is inserted.

The establishment of the grip 250 in the second (intermediate) grip position promotes the positioning of a leading edge 251 of grip 250 proximal to a second stop 446. The amount or distance of travel by grip 250 from the first to the second grip position may vary as contemplated by those skilled in the art. The positioning may be substantially placing the leading edge 251 of grip 250 in connection with the second stop 446. The configuration of the leading edge 251 may vary to promote the operational connection with second stop 446.

When grip 250 is in the second position it promotes a full tensioning of the first filament 480 and the nautilus member 450 reaching a secondary position. This secondary position of the nautilus member 450 further promotes the fully tensioned first filament 480 being in a substantially full engagement position with the nautilus member 450 by being substantially connected against and along the full top edge 452 of nautilus member 450. From this second positioning of the grip 250 it is described herein below that grip 250 can be further moved to a final position through continued rotational movement and travel down the grip guide 415. In exemplary embodiments for the current invention, this positioning of the grip 250 into a final position promotes the continued full tensioning of the first filament. This is accomplished by the configuration of the nautilus member 450 which provides a leading edge 451 that integrates with the leading edge 251 of grip 250. As the grip 250 rotates from the second to the third position the first filament 480 is placed in engagement with the leading edge 451 of nautilus member 450. Due to the angular orientation of the leading edge 451 in relation to the top edge 452 the tensioning force applied to first filament 480 is substantially prohibited from or does not continue to increase even as the grip 250 is moved from the second to the third position. This exemplary mechanism for applying and controlling the tensioning force applied to the first filament can be alternatively implemented utilizing various configurations and technologies as known and contemplated by those skilled in the art.

In FIG. 2C, the tip assembly 500 is shown as being established in a second deflected or articulated position, also referred to herein as the "S" position. The anterior tip movement and "C" shaping of tip assembly 500 shown in FIG. 2B is then followed by the articulation or bending of a second section 550 of tip assembly 500 in a secondary manner relative to the anteriorly bent first section 510. Second section 550 is capable of being articulated in the opposite forward or caudad direction (away from the center of curvature, denoted $\theta_2$ in FIG. 2C). This articulation of the second section 550 is an independent articulation relative to the articulation of first section 510. The articulation of second section 550 promotes and can achieve a final "S" shaped curve of TIP 500 and any device (endotracheal tube) within which the tip 500 of stylet 100 may be inserted. The deflection of this second section 550 of the tip 500 is achieved by the movement of the grip 250 from the intermediate position to a final grip position, thus completing the final grip and tip stroke.

This second deflected position is promoted and accomplished by engaging the grip 250 from the intermediate grip position and, through application of force to the grip 250, repositioning grip 250 to the final grip position. This movement of grip 250 promotes a second rotational force that is translated to a second shaping component 440 of the sequential tip shaping mechanism 400. In exemplary embodiments, the force applied to the grip is from a user. The user provides or applies a rotational force to grip 250. This user applied force can promote the further movement of grip 250 along the grip slot or guide 214 established by the housing assembly 200 in housing body 210. The user translated force through the grip 250 applies the second rotational force to a second stop 446 that is connected to the second shaping component 440. Through the second shaping component 440, which is connected to the second stop 446, the second rotational force applies a rotational force to a second filament connector 444 that is connected to the second shaping component 440. The second filament connector 444 is operationally connected with a first end 492 of a second filament 490. This operational connection, in the current embodiment, is provided by the first end 492 being established in a second filament first loop 493 configuration. The second filament first loop 493 is then wrapped around the second filament connector 444. Thus, as the second rotational force from engagement with grip 250 is translated into the rotational movement of second stop 446 a tensioning force is applied to the second filament first loop 493 to first end 492 of second filament 490. This tensioning force is translated along the length of second filament 490 to second end 496. A second filament second loop 497 configuration is established in second end 496. Second filament second loop 497 is configured to operationally connect and engage with second section 550 of tip 500. As the tensioning force applied to second filament 490 increases due to user engagement with grip 250, thereby moving grip 250 from the intermediate grip position to the final grip position, application of the second rotational force is translated into second section 550 of tip 500. This tensioning force causes the second filament second loop 497, through engagement with at least the shaping form 568, to apply a deflection force to second section 550 of tip 500. It is contemplated that second filament second loop 497 may apply a deflection force to second section 550 of tip 500 through engagement with any one or combination of shaping forms 561 through 568. The application of the deflection force to second section 550 causes tip 500 to articulate an angular amount, as denoted in FIG. 2B, from a second axis established by the tip 500 in the first deflected position. It is understood that the angle of articulation imparted to the second section 550 can vary and may be dependent on the amount of force applied to grip 250 by a user.

In exemplary embodiments, the tensioning forces applied to each of the first and second filaments is promoted, at least in part, through the connection of the filaments to the first filament connector 412 and second filament connector 446. Therefore, it is understood that the position of the first ends of the first and second filaments may be substantially promoted in a secure and static manner relative to the respective filament connectors within housing 210. It shall be further understood that the positioning of the first end 310 of shaft 305, when stylet 100 is in an operational enablement, is substantially proximal to or in contact with the first and second filament connectors in the first position. When tensioning forces are being applied to the first and second filaments it is useful or important that the shaft 305 remain in this positioning and not be moved or repositioned. Therefore, it is contemplated that within the housing proximal to the first and second filament connectors, an exemplary housing further comprises a mechanism or multiple mechanisms by which the position of the first end 310 of shaft 305, when shaft 305 is fully or partially inserted into an operational position within the housing 210, may be significantly affixed or promote the fixation of the position for shaft 305. In an exemplary embodiment one or more compression locking mechanisms may be included (not shown) in the housing and proximal to the first and second filament connectors. Thus, as the first end 310 of shaft 305 is inserted within the housing 210 through the shaft receiver 215 and approaches the first and second filament connectors any one or more of the compression locking component features may engage with the first end 310 or along any point of the shaft 305 proximal to and extending from the first end 310 to promote a securing of the position of shaft 305 within housing 210. The first end 310 of shaft 305 may further comprise significantly complementary component features that promote securing of the position of the shaft 305 when the first end nears the first and second filament connectors upon insertion in housing 210 by engagement with the compression locking component features established in the housing. It is contemplated that alternative connecting or locking mechanism may be employed to enable the securing of the position of a shaft when inserted through the shaft receiver into the housing of an exemplary embodiment of the stylet of the current invention.

The directionality, articulation or movement profile (geometry) of the tip 500 may be one which is pre-designated through a mechanism, such as the sequential handle motion as shown and described, one single lever motion, button press, handle squeeze, or it may be one which contains several mechanisms combined to perform independent actions of tip movement in independent directions. It is contemplated that the geometry of the tip for an exemplary stylet of the current invention may include articulation or movement capabilities along one or multiple axis. The operational connection of the handle assembly with the geometry of the tip may be provided by a manually driven mechanism or a mechanically driven mechanism. It is contemplated that the mechanically driven mechanism may be comprised of one or more component features, such as a motor, spring-loaded mechanism, hydraulic mechanism, semiconductors, and/or electronics. The manipulation of the tip may also be accomplished through the implementation of one or more automated mechanisms which may also be interfaced with various other devices, such as an onboard camera or external camera to perform hands free intubation.

Figure 5A:
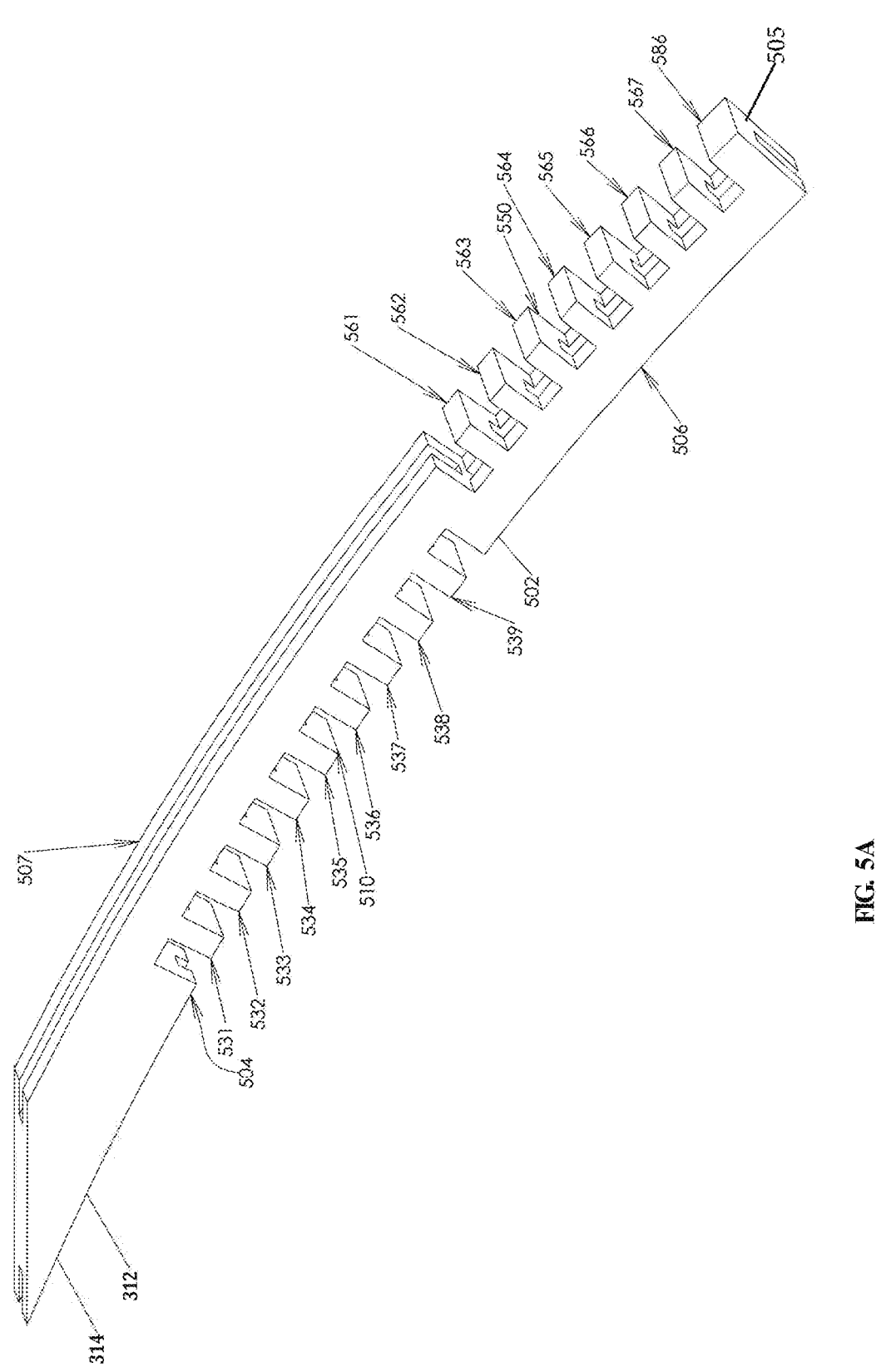
FIG. 5A is an illustration of the tip of the Stylet in accordance with an exemplary embodiment of the current invention.
Figure 5B:
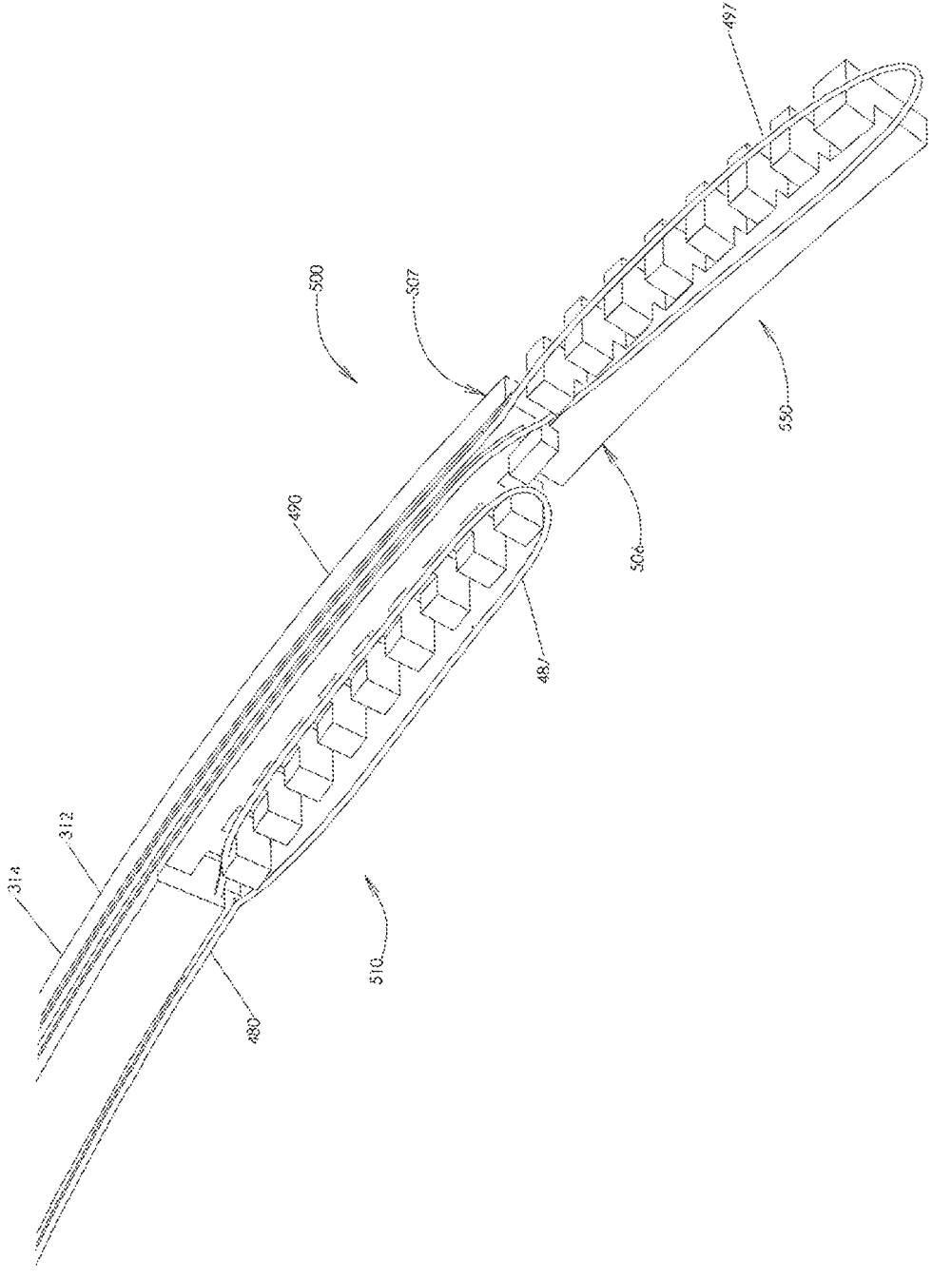
FIG. 5B is an illustration of the tip operationally engaged with a first and second manipulator of the sequential tip shaping mechanism of the Stylet in accordance with an exemplary embodiment of the current invention.

Tip assembly 500, shown in FIGS. 5A & 5B, is a sequentially directed articulating tip assembly that provides the movement capability as described herein for the current invention. The tip assembly 500 comprises a tip body 502 that connects on a first end 504 with the shaft assembly 300 and, opposite first end 504, is a second end 505 which is the leading edge for insertion of at least a portion of a stylet shaft within an endotracheal tube and intubation of a subject. It is contemplated that a mechanism is configured as part of the tip assembly 500 to secure the positioning of the tubing when the stylet is inserted within. The mechanism may comprise a compression locking and release means and technology. It is further contemplated that any mechanism for securing the position of the tubing could be configured exclusively in the shaft assembly 300 or such mechanisms may be employed in both the shaft (300) and tip (500) assemblies. Alternatively, various different mechanisms and technologies can be employed to promote the securing of the position of the tubing. This securing of positioning for the tubing is important during intubation procedures to promote the effective use of the stylet.

In the current embodiment, tip body 502 is integrally formed with shaft 305. Tt is contemplated that a tip assembly can be removably connected with a shaft assembly 300. Thus, it is contemplated that a tip assembly can be connected with multiple, different shaft assemblies and vice versa. The tip assembly 500 can be a flexible tip constructed or composed of malleable materials, such as polyethylene, polypropylene or a plastic where the composition of the material is controlled to promote flexibility for the tip body 502. It is contemplated that the composition and/or connection of the shaft is of similarly flexible or semi-flexible materials such as a semi-flexible plastic or of stainless steel. The mechanism is in operational connection with and can be interacted through the handle assembly.

A first section 510 of tip body 502 comprises articulation support forms 531 through 539 along the anterior side 506. A dorsal side 507 of this first section 510 comprises the continued extension of the second channel 340. The articulation support forms are established along the length of first section 510 and provides spacing between them. These forms and the spacing between them promote the deflection of this first section 510. The deflection capability is provided by the connection of first filament 480 with articulation support form 539. This connection is provided by the loop 487 wrapping around articulation support form 539. As described herein above in reference to FIGS. 2A-2C, deflection is promoted and accomplished when a tensioning force is applied to first filament 480 via user interaction with the handle assembly 200 and the sequential articulating tip mechanism 400.

A second section 550 of tip body 502 comprises articulation support forms 561 through 568 along the dorsal side 507. The anterior side 506 of this second section 550 comprises the continued extension of the first channel 320. The articulation support forms are established along the length of second section 550 and provides spacing between them. These forms and the spacing between them promote the deflection of this second section 550. The deflection capability is provided by the connection of second filament 490 with articulation support form 568. This connection is provided by the loop 497 wrapping around articulation support form 568. As described herein above in reference to FIGS. 2A-2C, deflection is promoted and accomplished when a tensioning force is applied to second filament 490 via user interaction with the handle assembly 200 and the sequential articulating tip mechanism 400.

It is contemplated that the tip assembly 500 of the current invention may be comprised of a single piece consisting of geometry allowing for the deflection of an endotracheal tube tip or may be comprised of multiple, independent bodies affixed to each other through some manner of mechanical mating. Further, the connection between any independent bodies or component features of the current invention may be made with joint mechanisms or such other movement capabilities as desired.

The shaft assembly 300 and tip assembly 500 of the invention can be inserted into tubes or sleeves of varying sizes and rigidities and fixtured to specific depths therein to manipulate along varying lengths of the tube. Because the tip assembly 500 of the stylet is able to manipulate the endotracheal tube end, the tip assembly 500 of the Stylet may also be comprised of geometry or linkages that achieve different curvature radii on the distal tube end. The tip assembly may also be structured in such a way that allows for distal tip movement of the endotracheal tube to be manipulated in a singledirection, in two or more directions independently or a combination of directions simultaneously.

It is contemplated that the shaft of the stylet may consist of multiple fixed or adjustable segments and lengths to serve as a manipulating stylet, also known as a Bougie. It is contemplated that the plurality of fixed or adjustable segments and lengths may promote the stylet (Bougie) moving in significantly anteriorly and/or posteriorly directions. Further, these multiple segments and lengths may promote a stylet (Bougie) having a varying length dimension ranging from six (6") inches to thirty-six (36") inches. These multiple segments and lengths can be connected using various connection technologies and mechanisms. In a stylet configuration the endotracheal tube along with the stylet are inserted simultaneously into the trachea as the tube end is manipulated in real time using the tip assembly. The stylet is first inserted into the trachea through manipulation of the tip and positioned in a central target location of the trachea where the endotracheal tube is then guided along the shaft to be inserted into the trachea.

The assemblies and/or mechanism(s) for movement of the tip assembly of the stylet may be comprised of various mechanical (i.e., spring-loaded), electrical, hydraulic and other mechanisms to provide tip deflection as may be contemplated by those skilled in the art. By way of non-limiting examples, it is contemplated that the mechanism(s) may include the use of one or more, alone or in any combination, a string, twine, wire, spring, filament, tubing, or may be a sealed hydraulic mechanism, an electrically charged mechanism, or magnetic mechanism, that enables, promotes and/or allows the deflection of the tip as has been described based on the manipulation of the handle mechanism.

It is contemplated for exemplary embodiments of the current invention that the tip of the stylet may also contain geometry which allows for a pre-determined deflection of a portion of the endotracheal tube which is the tube tip inserted into a subject. This can include a deflection of a first portion of the tube tip in an anterior direction to the subject followed by a forward deflection of a second portion of the tube tip relative to the anteriorly bent first portion. This motion can either be sequentially pre-determined or independently operated by the handle mechanism. The handle may contain a sequential tip articulation mechanism, implemented as a cam mechanism, which upon manipulation of the handle will move the tip in the intended movements described above.

Another exemplary embodiment of stylet 600 is shown in FIG. 6. Stylet 600 comprises a handle mechanism configured in an alternative manner to that shown in stylet 100 but that provides a similar sequential tip articulation functionality as has been described herein. The handle mechanism further includes a secondary grip to promote an improved user interaction with the stylet 600. It is further contemplated that this secondary grip may promote an improvement in the operational performance of the stylet. Additionally, an exemplary stylet device may include or comprise three of more handle or grip assemblies. The handle mechanism connects, in operational engagement, with a first end of the shaft assembly and includes an assembly by which the stylet applies tensioning forces to the tip (second end) of the shaft assembly enabling articulation of the tip. This articulating capability enabling the "C" and "S" forming of the tip, and any tubing within which the stylet is inserted, in a similar manner as has been described herein.

Figure 7:
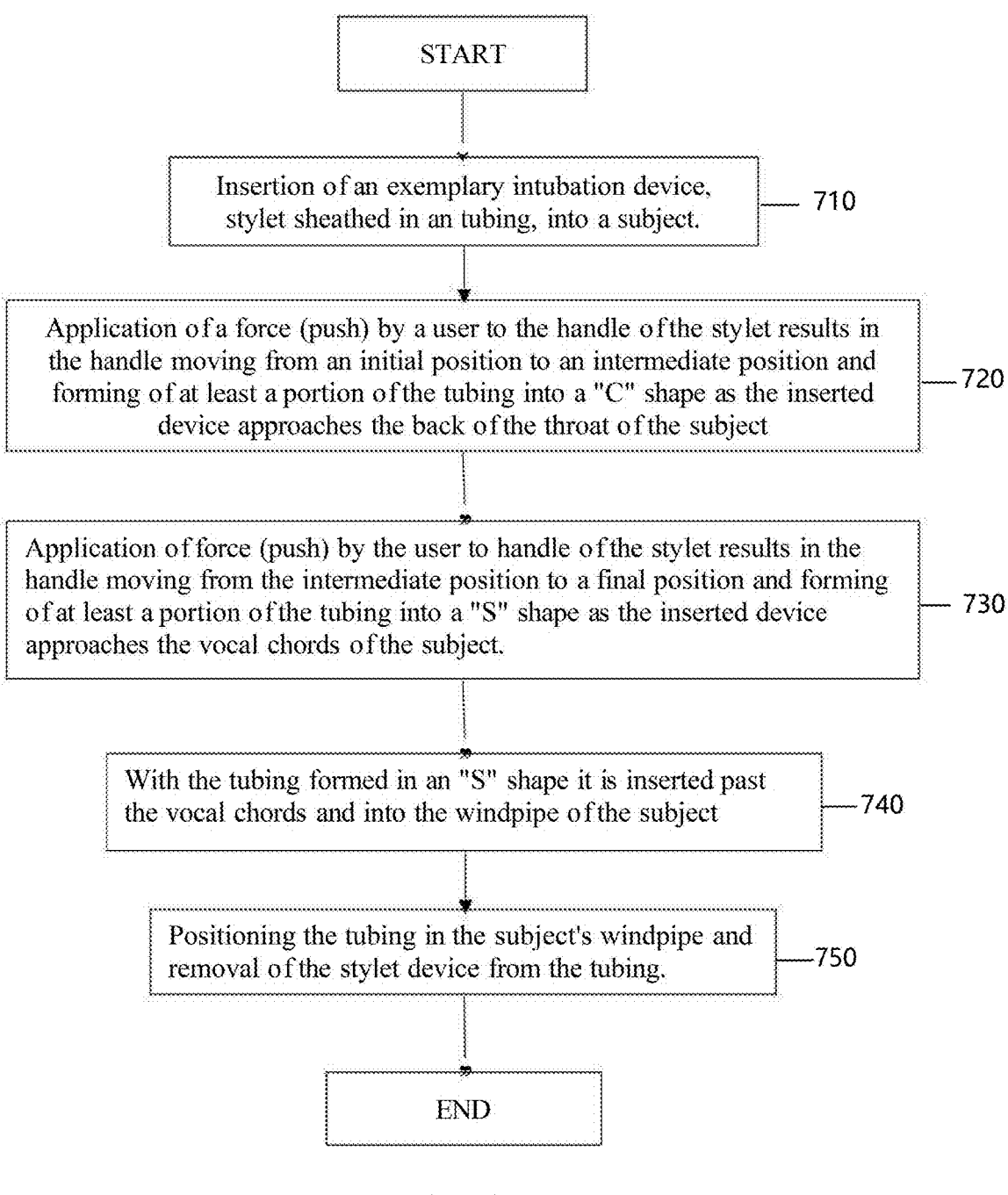
FIG. 7 is a block diagram illustrating a method for intubation in accordance with an exemplary embodiment of the current invention.

An exemplary intubation process 700 using an exemplary stylet device of the current invention is shown in FIG. 7. By employing a stylet device of the current invention inserted within an endotracheal tube the intubation process begins with the insertion of the tip assembly into a tubing forming an exemplary intubation device, commonly referred to as a Bougie, and then insertion of the Bougie, tip assembly leading, into a subject in first step 710. During the intubation process, as the tip assembly, sheathed in the tubing, reaches the back of the throat of the subject a user of the stylet in a second step 720 can apply a first force (push) on the handle. This first force application occurs in real time with the stylet still inserted within the subject and may occur in conjunction with a user attempting to insert the stylet further within the subject. The user pushing on the handle results in the handle being moved from its initial, rest position to an intermediate or a second position. As described herein, this movement of the handle further results in the application of a first tensioning force to at least a portion (e.g., first segment) of the tip assembly. The application of the first tensioning force to this portion of the tip assembly results in the deflection or articulation of the tip assembly. This deflection promotes and can accomplish the formation of the tip assembly into what is referred to as a "C" shape, as has been described. This shaping functionality can enable the bending of the tubing, at least in the portion of the tubing proximally or generally located in position relative to this deflected portion of the tip assembly, into a generally "C" shape which can promote an increase in the ease of inserting the tubing and, thereby, effectiveness in accomplishing intubation of the subject. As described, the user of the stylet can adjust the angle of deflection established for the tip assembly by varying the amount of force they apply to the handle.

In the next step 730, as the intubation process proceeds and in real time the tubing continues to be further inserted into the windpipe of the subject, the user of the stylet can apply a second tensioning force to the tip assembly by continuing to engage with the handle. The user, by applying a second force (push) to the handle, moves the handle from the intermediate position to a final or fully activated position to promote and achieve the application of the second tensioning force. As described herein, this movement of the handle into the final position results in the application of the second tensioning force to another portion (e.g., second segment) of the tip assembly. The applied second tensioning force promotes and accomplishes a deflection of this portion of the tip assembly. The deflection of this portion of the tip assembly results in the formation of the tip assembly into what has been described herein and is referred to as an "S" shape. Thus, this shaping functionality can enable the bending of the tubing, at least in the portion of the tubing proximally or generally located in position relative to this deflected portion of the tip assembly, into a generally "S" shape which can promote an increase in the ease of inserting the tubing and, thereby, effectiveness in accomplishing intubation of the subject. Generally, this forming of the tubing into the "S" shape in real time during the intubation procedure is particularly advantageous when the tip assembly is approaching the vocal chords of the subject. With the tubing formed into the "S" shape, in a next step 740, a user of the stylet can continue by further inserting at least a portion of the tip assembly past or through the vocal chords in a subject's windpipe. This insertion past the vocal chords is significantly improved by the current invention which allows a user to deflect the tubing in real time during the intubation, thereby, enabling the user to adjust the position of the tip assembly to promote an increase in a user's ability to effectively address the anatomical conditions present in the subject. In a final step 750, the tubing is positioned in the windpipe and the stylet device is removed from within the tubing.

The improved capabilities of the current invention promote a more efficient and effective process of intubation for a subject and significantly reduce if not altogether remove the need for a user to remove the breathing tube from the mouth or nose to reshape it and then reinsert during the intubation process. Thus, the current invention can significantly avoid these types of time-consuming delays that can result in damage to the oral tissues, drop in oxygen levels and with each attempt, the likelihood of a successful intubation decreases. The current invention promotes a minimizing of these types of complications and can significantly reduce or prevent episodes of cardiac arrest, brain injury, death, and with the recent pandemic, the spread of pathogens. Thus, the current invention may promote a reduction in the deaths associated with intubation due to lack of oxygenation which has been estimated to range from 2-3%. The current invention may further promote an increase in the successful intubations that occur on the first attempt, thereby, improving on the up to 40% failure rate that has been estimated for first attempts.

The exemplary embodiments of the stylet device of the current invention can be used in conjunction with various additional materials. For instance, the stylet may be used with various lubricious, sterilized, biocompatible and/or biodegradable materials. These materials, in combination with the stylet, can promote an increase in the success and optimal intubation procedures. It is further understood that these materials may further promote the interchangeable configuration(s) described herein for exemplary embodiments of the current invention. Where a component feature of an exemplary stylet device has become non-functional that feature can be removed from the stylet and a replacement, secondary component feature can be connected. For instance, a shaft and/or tip assembly may have to be replaced and then use of the stylet made in an emergent situation with subjects in need of intubation. In these circumstances the application of sterilizing and/or lubricious materials may be critically important to promote the subject's health and an improved intubation process.

To further promote the improved performance provided by the exemplary embodiments of the current invention, the tip assembly may also be configured to include a camera, a light, a suction channel, electrodes, and sensors which provide feedback to the user to easily and rapidly insert the stylet tip into the trachea. Still further, means may be configured in a stylet for administering oxygen or anesthesia. A pressure sensor may be included in a stylet to detect the tip coming into contact with tissue. It is contemplated that an exemplary stylet that includes electrodes and/or sensor can be understood as configured to transmit and/or receive signals, such as a frequency that may be one or more terahertz frequencies. An exemplary sensor can be configured to detect and provide an indication of the presence of one or more gases including, without limitation, oxygen and/or carbon dioxide. It is further contemplated that the stylet can be in a generally catheter configuration and/or include an electronic frequency transmission mechanism including, without limitation, a wire. The electronic frequency transmission mechanism can provide the capability of transmitting and/or receiving various signals, such as various terahertz frequencies, as part of an exemplary stylet configuration. These features may be permanently affixed to the tip or along the stylet shaft, may be detachable, or adjustable. These various features may enable the stylet for use in various areas of a subject's body and promote or assist with diagnosis and treatment of tissue abnormalities. It is further contemplated that component features, assemblies, mechanisms and the like configured for the exemplary embodiments of the current invention can comprise one or multiple parts that can be integrally formed or connected with and removable from one another. Thus, the interchangeability of these features promote an ease of use of the current invention and ability to reconfigure when desired by a user.

Deviations may be made from the specific embodiments disclosed in the specification without departing from the spirit and scope of the invention. The illustrations and discussion herein has only been provided to assist the reader in understanding the various aspects of the present disclosure. While this disclosure contains many specifics, these should not be construed as limitations on the scope of the disclosure or of what may be claimed, but rather as descriptions of features specific to particular embodiments of the disclosure. Certain features that are described in this specification in the context of separate embodiments and/or arrangements can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Additionally, the foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A stylet device, comprising:
a handle assembly housing a sequential tip shaping mechanism;
a shaft assembly having a first end connected to the handle assembly; and
a tip assembly connected to a second end of the shaft assembly,
wherein the sequential tip shaping mechanism enables the manipulation of a geometry of the tip assembly.

2. The stylet of claim 1, wherein the tip assembly comprises at least one of a camera, a light, a suction channel, electrodes and sensors.

3. The stylet of claim 1, wherein the stylet is configured to administer at least one of oxygen, treatment medication, suction or anesthesia.

4. The stylet of claim 1, wherein the stylet comprises at least one interchangeable handle assembly, shaft assembly and tip assembly, and at least one of the shaft assembly and tip assembly is comprised of a sufficiently malleable material for articulation of the stylet.

5. The stylet of claim 4, wherein the tip assembly comprises sufficiently malleable material allowing articulation of at least one of a first and second section of the tip assembly relative to at least one of one another and the shaft assembly.

6. The stylet of claim 1, wherein the shaft assembly comprises at least one of multiple fixed or multiple adjustable segments, and has a length ranging from six inches to thirty-six inches.

7. The stylet of claim 1, wherein the stylet comprises at least one sensor, catheter and wire configured to transmit one or more terahertz frequencies.

8. The stylet of claim 1, wherein the stylet comprises one or more materials selected from at least one lubricious, sterilized, biocompatible and biodegradable materials.

9. The stylet of claim 1, wherein the sequential tip shaping mechanism is configured to manipulate the geometry of the tip assembly in a single direction, in two or more directions independently, or in a combination of directions simultaneously.

10. The stylet of claim 1, wherein at least one of the shaft assembly and tip assembly is inserted into a tube or a sleeve.

11. A stylet device, comprising:
a handle assembly housing a sequential tip shaping mechanism;
a shaft assembly comprising a first section connected at a first end to the handle
assembly, an intermediate section connected at a first end with a second end of the first section; and
an articulable tip assembly connected to a second end of the intermediate section,
wherein the sequential tip shaping mechanism enables the manipulation of a geometry of at least one of a first and second section of the tip assembly and the shaft assembly.

12. The stylet of claim 11, wherein the tip assembly comprises at least one of a camera, a light, a suction channel, electrodes and sensors.

13. The stylet of claim 11, wherein the stylet is configured to administer at least one of oxygen, treatment medication, suction or anesthesia.

14. The stylet of claim 11, wherein the stylet comprises at least one interchangeable handle assembly, shaft assembly and tip assembly and the shaft assembly comprises at least one of multiple fixed or multiple adjustable segments, and has a length ranging from six inches to thirty-six inches.

15. The stylet of claim 11, wherein one or more malleable materials form at least one of the tip assembly, shaft assembly and handle assembly.

16. The stylet of claim 15, wherein the tip assembly comprises sufficiently malleable material allowing articulation of the at least one first and second section of the tip assembly relative to at least one of one another and the shaft assembly.

17. The stylet of claim 11, wherein the stylet comprises at least one sensor, catheter and wire configured to transmit one or more terahertz frequencies.

18. The stylet of claim 11, wherein the stylet comprises one or more materials selected from at least one lubricious, sterilized, biocompatible and biodegradable materials.

19. The stylet of claim 11, wherein the sequential tip shaping mechanism is configured to manipulate the geometry of the tip assembly in a single direction, in two or more directions independently, or in a combination of directions simultaneously.

20. The stylet of claim 11, wherein at least one of the shaft assembly and tip assembly is inserted into a tube or a sleeve.

* * * * *